US00PP32242P2

(12) United States Plant Patent
Dirr et al.

(10) Patent No.: US PP32,242 P2
(45) Date of Patent: Sep. 29, 2020

(54) ***HYDRANGEA* PLANT NAMED 'COF-HM2'**

(50) Latin Name: *Hydrangea macrophylla*
Varietal Denomination: COF-HM2

(71) Applicants: Michael Dirr, Bogart, GA (US); Mark Griffith, Watkinsville, GA (US)

(72) Inventors: Michael Dirr, Bogart, GA (US); Mark Griffith, Watkinsville, GA (US)

( * ) Notice: Subject to any disclaimer, the term of this patent is extended or adjusted under 35 U.S.C. 154(b) by 0 days.

(21) Appl. No.: 16/602,146

(22) Filed: Aug. 14, 2019

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 6/48
See application file for complete search history.

*Primary Examiner* — Anne Marie Grunberg
(74) *Attorney, Agent, or Firm* — Cassandra Bright

(57) ABSTRACT

A new and distinct cultivar of *Hydrangea* plant named 'COF-HM2' is disclosed, characterized by vigorously growing, compact plants with strong, upright peduncles. Inflorescences are dense mophead with uniquely colored sepals beginning maturing green-purple and maturing pink. Sepals are extremely thick and persist in good condition up to 8 weeks. Fall foliage is a deep red. The new variety is a *Hydrangea*, normally produced as an ornamental plant.

6 Drawing Sheets

Latin name of the genus and species: *Hydrangea macrophylla.*

Variety denomination: 'COF-HM2'.

BACKGROUND OF THE INVENTION

The new *Hydrangea* cultivar was found and selected as a naturally-occurring whole plant mutation in a garden setting in Bishop, Ga., during July of 2018. The parent variety is the unpatented *Hydrangea* 'Greenmantle'.

Asexual reproduction of the new cultivar 'COF-HM2' by vegetative soft wood cuttings was first performed during July of 2018, at a commercial greenhouse in Watkinsville, Ga. Subsequent propagation has shown that the unique features of this cultivar are stable and reproduced true to type in successive generations.

SUMMARY OF THE INVENTION

The cultivar 'COF-HM2' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'COF-HM2' These characteristics in combination distinguish 'COF-HM2' as a new and distinct *Hydrangea* cultivar:

1. Inflorescences emerge green, maturing green, spotted, mottled, blotched, and streaked with purple or pink. Sepals most often maintain this color into maturity. Blueing is difficult. Tests with combinations of aluminum sulfate and blue max (slow release aluminum sulfate) had resulted in minimal success. Plant is commercially valuable without blueing.

2. Sepals extremely thick. Persisting in good condition up to 8 weeks and more with rich color retention in USDA Zone 8.
3. Inflorescences do not wilt/flag like typical *Hydrangea macrophylla* in the heat of zone 8.
4. Lustrous rich green foliage turns shades of red in autumn.
5. Foliage is highly resistant to powdery mildew. Moderately resistant to *Cercospora* leaf spot. *Cercospora* will develop but spots do not enlarge and destroy the foliage appearance.
6. Compact habit with strong stems holding the inflorescences upright.
7. Vigorous growth habit.

PARENTAL COMPARISON

Plants of the new cultivar 'COF-HM2' is similar to the parent variety *Hydrangea macrophylla* 'Greenmantle', unpatented in most horticultural characteristics. However 'COF-HM2' differs in the following:

1. The new variety exhibits more vigorous growth.
2. The new variety propagates easier and has a faster production cycle.
3. The new variety produces flower of a different color, having more pink tones, compared to the lavender mauve tones seen in the parent.

COMMERCIAL COMPARISON

Plants of the new cultivar 'COF-HM2' can be compared to the variety *Hydrangea macrophylla* 'Bailmer', U.S. Plant Pat. No. 15,298. These varieties are similar in most horticultural characteristics; however 'COF-HM2' differs in the following:

1. The new variety grows approximately 20% faster than this comparator.

2. The new variety produces thicker sepals than this comparator.
3. The new variety produces sepals colored pink and mottled green, sepals of this comparator are pink with a white base.
4. Individual inflorescences of the new variety are longer lasting than those of this comparator.

BRIEF DESCRIPTION OF THE PHOTOGRAPHS

The accompanying photograph in FIG. 1 illustrates in full color a typical inflorescence of 'COF-HM2' in the emerging stage, having no aluminum treatment.

Figure 1:
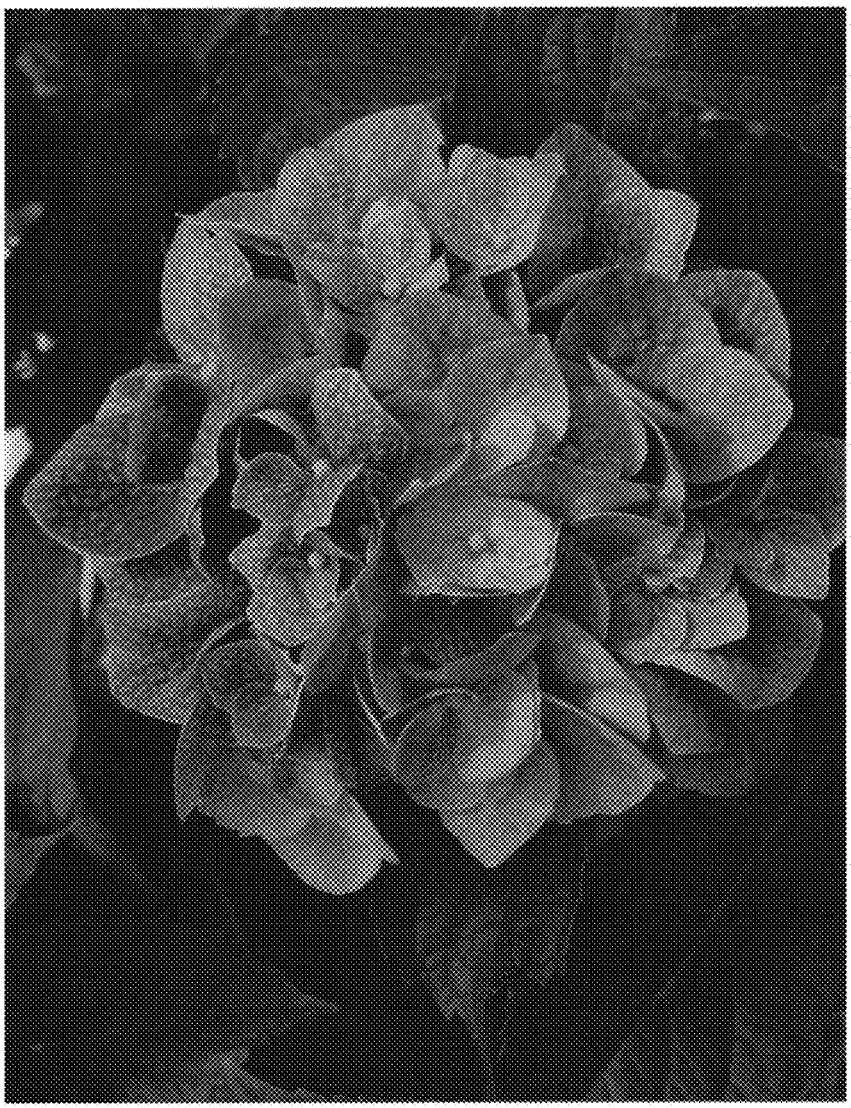
Figure 2:
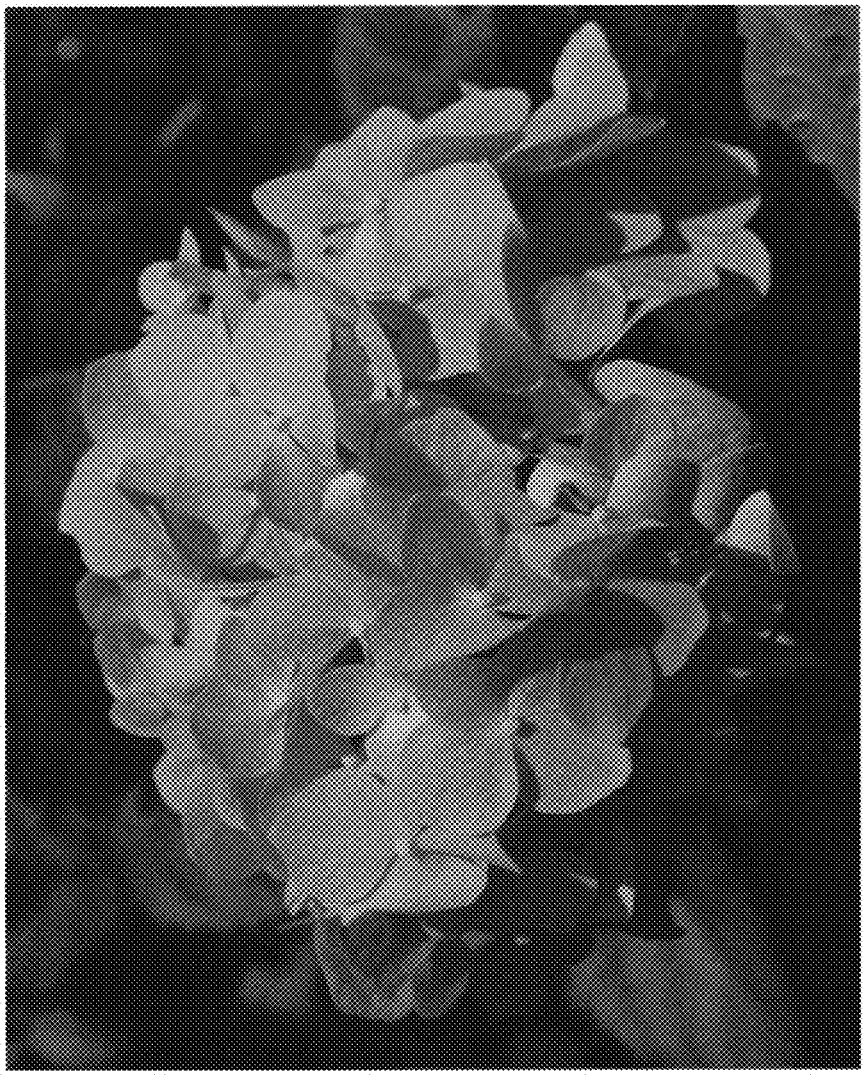
FIG. 2 illustrates a typical inflorescence of 'COF-HM2' in the mature stage, having no aluminum treatment.
Figure 3:
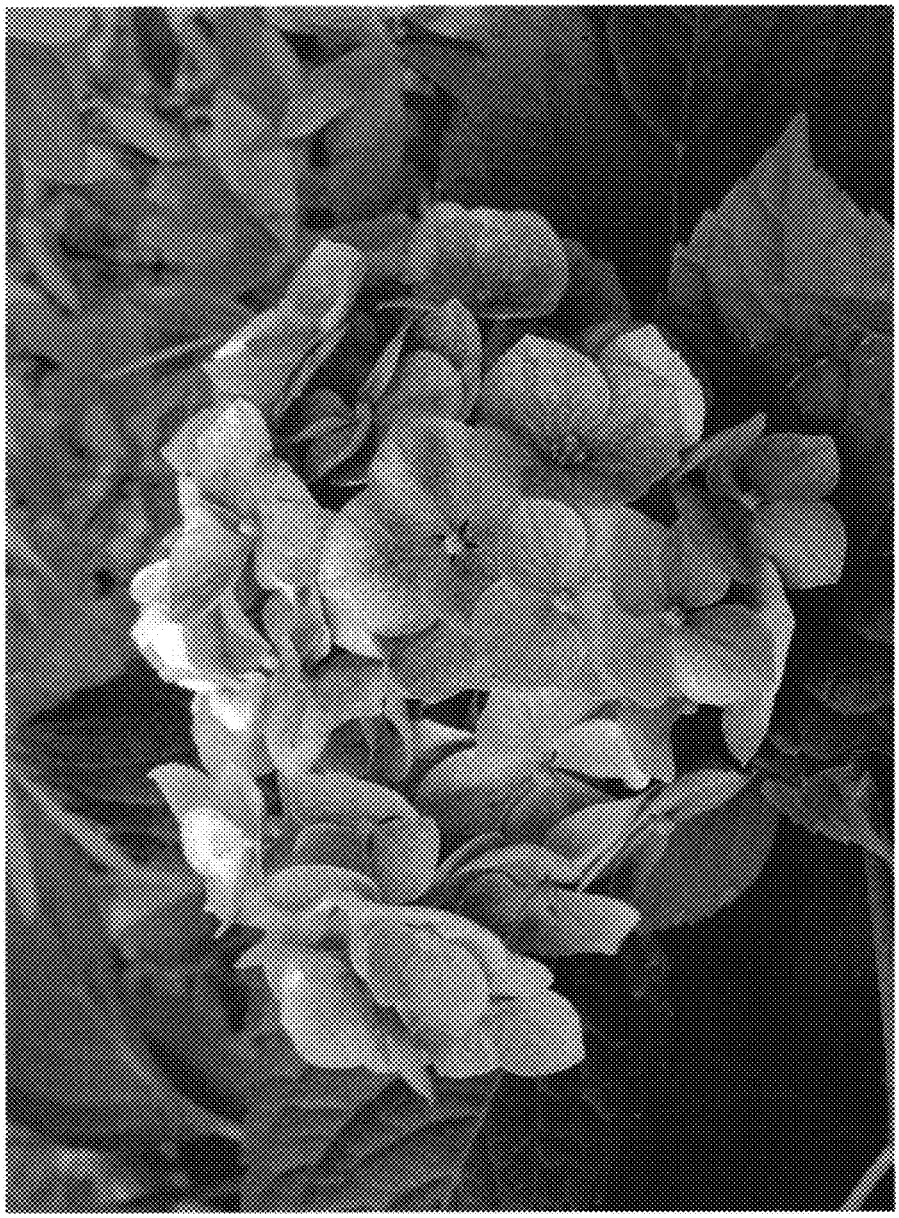
FIG. 3 illustrates an inflorescence in the transitional stage between immature and mature, given a typical aluminum sulfate treatment of 70 grams top dressed.
Figure 4:
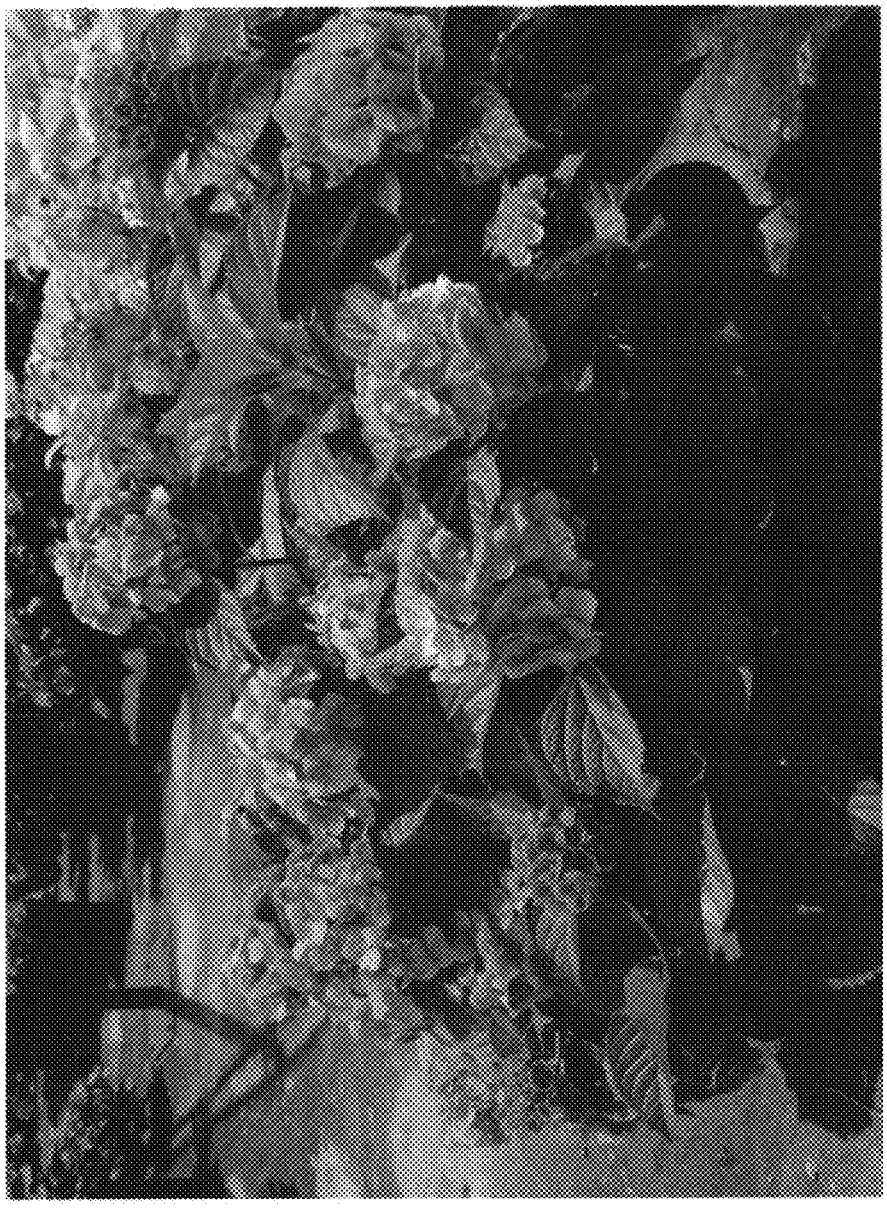
FIG. 4 illustrates in full color a typical plant of 'COF-HM2' in a 10 gallon pot, having no aluminum treatment, with multiple inflorescences at various stages of maturity. The plant in the photograph is approximately 18 months old, in a 10-gallon pot.
Figure 5:
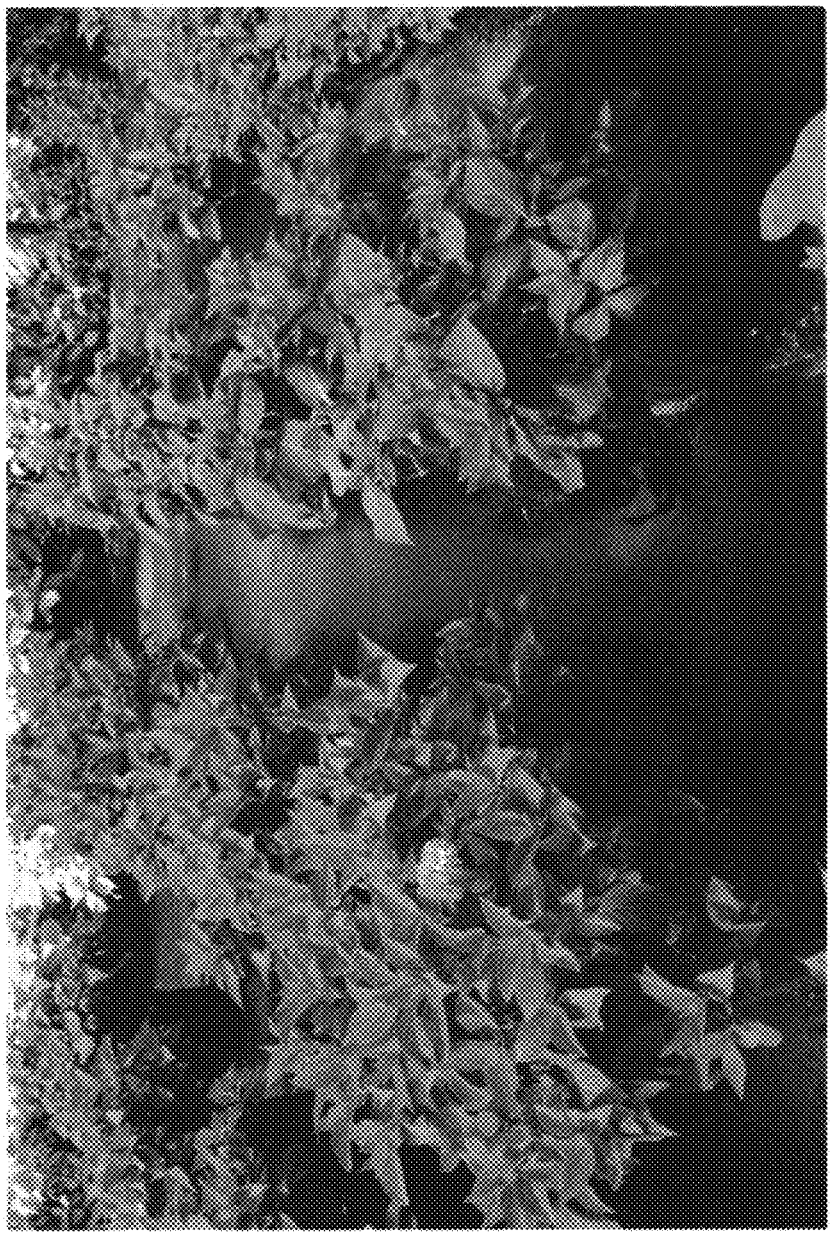

FIG. 5 illustrates the increased growth rate of the new variety. The plant of the left of the figure is the new variety, the row of plants on the right of the figure is the comparator 'Bailmer'. Plants illustrated in FIG. 5 are the same age and cultivated under identical growing conditions.

Figure 6:
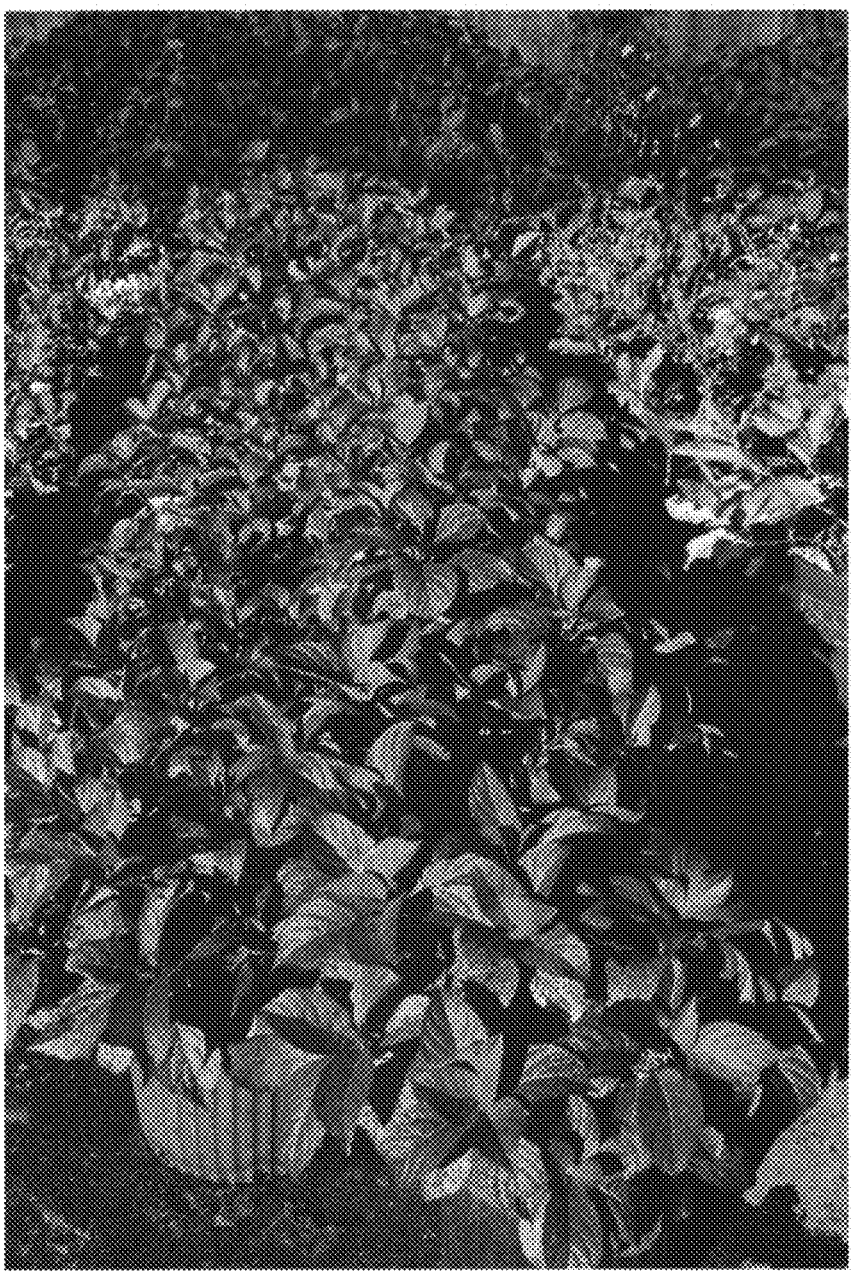

FIG. 6 illustrates plants of the new variety during Fall, with the distinctive Fall foliage coloration.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'COF-HM2' plants grown in a commercial greenhouse in Watkinsville, Ga., outdoors under 50% saran shade. Measurements were taken during May of 2019. The plants were about 18 months old planted in 10-gallon pots. The growing temperature ranged from 15° C. to 25° C. during the day, and 10° C. to 15° C. at night. Measurements and numerical values represent averages of typical plant types.

Botanical classification: *Hydrangea macrophylla* 'COF-HM2'.

PROPAGATION

Time to rooting: 21 to 28 days at approximately 20° to 25° C.

Time to produce a flowering plant: 1 year to produce a full, flowering plant from a rooted cutting.

PLANT

Growth habit: Dense, compact.
Overall plant shape: Rounded to broad rounded.
Height: Approximately 60 cm.
Plant spread: Approximately 80 cm.
Growth rate: Rapid.
Branching characteristics:
Length of lateral branches/stems: Approximately 45 cm.
Number of lateral branches: Approximately 35.
Diameter of lateral branches: Approximately 0.7 cm.
Pinching required: Yes. Prune 2 to 3 times in production cycle.
Lateral branch shape: Round.
Lateral branch strength: Moderate to strong.
Lateral branch/stem color: Near RHS Yellow-Green 144B.
Branch angle: 25° to 30°.
Other stem or plant characteristics:
*Lenticel length.*—Approximately 2 mm.
*Lenticel width.*—Approximately 0.5 mm.
*Lenticel color.*—Near RHS Grey-Brown N199B.
Number of leaves per lateral branch: Average 16.
Root description: Profuse, diffuse, well branched, RHS White 155D.
Age of plant described: Approximately 18 months from a rooted cutting.

FOLIAGE

Leaf:
*Arrangement.*—Opposite.
*Compound or single.*—Single (simple leaf).
*Average length.*—Approximately 15 cm.
*Average width.*—Approximately 9 cm.
*Shape of blade.*—Ovate.
*Lobing.*—None.
*Apex.*—Acuminate.
*Base.*—Cuneate.
*Attachment.*—With petiole.
*Margin.*—Serrate.
*Texture of top surface.*—Waxy, smooth, veins impressed.
*Texture of bottom surface.*—Rough, veins extruded.
*Leaf internode length.*—Approximately 6 cm.
*Color.*—Young foliage upper side: Near RHS Green 137B. Young foliage under side: Near RHS Green 137C. Mature foliage upper side: Near RHS Green 137A. Mature foliage under side: Near RHS Green 137C. Fall foliage upper side: Near RHS Greyed-Purple 185B, flushed 183C, base near Green 137C. Fall foliage under side: Near RHS Greyed-Purple 185C, base near Green 138B.
*Venation.*—Type: Pinnate. Venation color upper side: Near RHS Green 143B. Venation color under side: Near RHS Yellow-Green 147C.
*Durability of foliage to stresses.*—Moderate to high.
Petiole:
*Average length.*—Approximately 3.5 cm.
*Diameter.*—Approximately 4 mm.
*Texture.*—Relatively stout.
*Color.*—Near RHS Yellow-Green 144B.

FLOWER

Bloom period:
*Natural season.*—May to June.
*Flowering continuous, sporadic, intermittent, or other.*—Sporadic after major period.
Inflorescence:
*Type.*—Corymb.
*Shape.*—Rounded-globose.
*Height.*—Approximately 10 cm.
*Width.*—Approximately 15 cm.

*Quantity of flowers per inflorescence*.—Fertile flowers: Few to none. Sterile Flowers: Approximately 65.

Bud:

*Bud shape*.—Round.
*Bud length*.—Approximately 2 mm.
*Bud diameter*.—Approximately 2 mm.
*Bud color*.—Near RHS Yellow-Green 144C.
*Base/calyx*.—Near RHS Yellow-Green 144C.

Sterile flowers: Petals less than 1mm, reduced and not observed to open.

Sterile flower sepal:

*Arrangement*.—Cruciform to rotate overlapping.
*Number*.—3 to 5 per cluster.
*Shape*.—Broad ovate to rounded.
*Tip*.—Abruptly broad acute.
*Base*.—Rounded.
*Margin*.—Entire.
*Length*.—1.5 cm.
*Width*.—1.5 cm.
*Texture, upper*.—Glabrous.
*Texture, lower*.—Glabrous.
*Color*.—Upper surface at first opening: Acidic: Near RHS Blue 101B. Basic: Earliest stage Purple 75D with veins Green 143B. Changes to near RHS Purple 75A over Green 143C. Upper surface at maturity: Acidic: Near RHS Blue 101B. Basic: Near RHS Red-Purple 73B. Under surface at first opening: Acidic: Near RHS Blue 100C. Basic: Earliest stage Purple 75D with veins Green 143C. Changes to near RHS Purple 75C. Under surface at maturity: Acidic: Near RHS Blue 100D. Basic: Near RHS Purple 75D. Fading to Upper surface: Acidic: Near RHS Blue 100B. Basic: Near RHS Red-Purple 69A. Fading to Under surface: Acidic: Near RHS Blue 100D. Basic: Near RHS Red-Purple 69D.

Sterile flower pedicel:

*Length*.—1.3 cm.
*Diameter*.—1 mm.
*Angle*.—30°.
*Strength*.—Flimsy.
*Texture*.—Fine.
*Color*.—Acidic: Near RHS Violet-Blue 91B. Basic: Near RHS Red-Purple 68D.

Fertile flower:

*Bud shape*.—Round.
*Bud length*.—2 mm.
*Bud diameter*.—3 mm.
*Bud color*.—Acidic: Near RHS Blue 100C. Basic: Near RHS Green 135D.
*Flower aspect*.—Not showy.
*Flower shape*.—Star-shaped.
*Flower length*.—3 mm.
*Flower diameter*.—5 mm.
*Flower depth*.—2 mm.
*Self-cleaning/persistent*.—Appear to be self-cleaning.

Fertile flower petals:

*Length of petal*.—2 mm.
*Width of petal*.—1.5 mm.
*Apex*.—Rounded.
*Shape of petal*.—Obovate.
*Petal margin*.—Entire.
*Petal arrangement*.—Five petals, actinomorphic.
*Petal number*.—5.
*Petal base*.—Cuneate.
*Petals fused*.—Free.
*Petal texture*.—Fine.
*Color*.—Upper surface at first opening: Acidic: Near RHS Green 142B. Basic: Near RHS Green 142B. Upper surface at maturity: Acidic: Near RHS Blue 100B. Basic: Near RHS Red-Purple 73B. Under surface at first opening: Acidic: Near RHS Green 142C. Basic: Near RHS Green 142C. Under surface at maturity: Acidic: Near RHS Blue 100C. Basic: Near RHS Red-Purple 73C. Upper surface fading to: Acidic: Near RHS Blue 100D. Basic: Near RHS Red-Purple 73D. Lower surface fading to: Acidic: Near RHS Blue 100D. Basic: Near RHS Red-Purple 73D.

Fertile flower sepal:

*Arrangement*.—Solitary.
*Number*.—5.
*Shape*.—Star-shaped.
*Tip*.—Acute.
*Base*.—Truncate.
*Margin*.—Entire.
*Length*.—1 mm.
*Width*.—1 mm.
*Texture, upper*.—Fine.
*Texture, lower*.—Fine.
*Color*.—Upper surface at first opening: Near RHS Blue 101C. Upper surface at maturity: Near RHS Blue 101C. Under surface at first opening: Near RHS Blue 101D. Under surface at maturity: Near RHS Blue 101C. Upper surface fading to: Near RHS Blue 101C. Lower surface fading to: Near RHS Blue 101C.

Fertile flower pedicel:

*Angle*.—40°.
*Strength*.—Moderate.
*Length*.—3 mm.
*Width*.—Less than 1 mm.
*Texture*.—Fine.
*Color, same basic or acidic*.—Near RHS Violet-Blue 98B.

Peduncle:

*Length*.—Approximately 4 cm.
*Diameter*.—Approximately 3 mm.
*Texture*.—Medium.
*Angle*.—70°.
*Strength*.—Strong.
*Color*.—Near RHS Blue 100C.

REPRODUCTIVE ORGANS

Sterile flower: Not observed.

Fertile flower:

*Stamen number*.—10.
*Filament length*.—3 mm.
*Filament color*.—Near RHS Blue 101C.
*Anther shape*.—Oblong.
*Anther length*.—1 mm.
*Anther color*.—Near RHS Blue 101C.
*Pollen amount*.—Present but minimal.
*Pollen color*.—Near RHS White 155B.

Gynoecium:

*Pistil number*.—1.
*Pistil length*.—2 mm.
*Stigma shape*.—Flattened.
*Stigma color*.—Near RHS Blue 101C.
*Style length*.—Less than 1 mm.

*Style color*.—Near RHS Blue 101C.
*Ovary color*.—Near RHS Blue 101C.

OTHER CHARACTERISTICS

Fruit/seed production: Not observed.
Disease resistance: Neither resistance no susceptibility to normal diseases and pests of *Hydrangea macrophylla*.

Drought tolerance and cold tolerance/temperature range: Similar to most *H. macrophylla*. Cold tolerance unconfirmed.

What is claimed is:

1. A new and distinct cultivar of *Hydrangea* plant named 'COF-HM2' as herein illustrated and described.

* * * * *